United States Patent [19]

Diebold

[11] Plant 4,171

[45] Dec. 27, 1977

[54] PEACH TREE-MUTATION OF RIO OSO GEM VARIETY

[75] Inventor: David A. Diebold, Kelso, Mo.

[73] Assignee: Stark Brothers Nurseries & Orchards Company, Louisiana, Mo.

[21] Appl. No.: 751,727

[22] Filed: Dec. 17, 1976

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Burns, Doane, Swecker & Mathis

[57] ABSTRACT

A new and distinct peach tree variety which originated as a whole tree mutation of the Rio Oso Gem variety (U.S. Plant Pat. No. 84) is provided. The fruit of the new variety ripens approximately 17 to 18 days earlier than that of the Rio Oso Gem variety and approximately 8 days earlier than that of the Early Rio Oso Gem variety (U.S. Plant Pat. No., 2940).

2 Drawing Figures

SUMMARY OF THE INVENTION

The new and distinct variety of peach tree was discovered in 1961 as a bud sport of the Rio Oso Gem variety (U.S. Plant Pat. No. 84) at Diebold's Orchard, Inc. maintained on cultivated property in Scott County, Mo.

The fruit of the new variety is indistinguishable from that of the Rio Oso Gem variety. It has an identical size, color, texture, flavor, and tendency to produce raised sutures. However, the fruit ripens approximately 17 to 18 days earlier than that of the Rio Oso Gem and approximately 8 days earlier than that of the Early Rio Oso Gem (U.S. Plant Pat. No. 2,940). The tree of the new variety additionally displays more vigor and disease resistance and smaller flowers than the Rio Oso Gem variety.

The new variety exhibits good resistance to disease. This improved disease resistance of the new variety has been confirmed by observing the new variety while growing in an orchard where trees of the Rio Oso Gem variety were nearby. Bacterial leaf spot was encountered in the Rio Oso Gem variety, but was absent in the new variety.

Because of the distinctive characteristics of the new variety the plant was asexually reproduced by budding. This propagation shows that the unique combination of characteristics comes true to form and is established and transmitted in succeeding propagation. The specimens described herein were grown and observed at Scott County, Mo.

BRIEF DESCRIPTION OF THE DRAWINGS

FIG. 1 shows typical specimens of the fruit and foliage of my new variety as depicted in color. As previously indicated the fruit color including that of the fruit flesh is believed to be identical to that of the Rio Oso Gem variety. Accordingly, the actual fruit flesh color tends to be of a more yellow color than that manifest in FIG. 1.

FIG. 2 illustrates in a more accurate manner the flesh color of the fruit of the new variety.

DETAILED DESCRIPTION OF THE NEW VARIETY

Dates of First and Last Picking: July 26, 1976 and Aug. 2, 1976, respectively.

Tree: Large; vigorous; dense; spreading; vase formed; half hardy; productive; regular bearer.

*Trunk.*—Medium stocky; smooth.

*Branches.*—Medium stocky; medium smooth. Color — 2 year wood — brown — Amber Brown Plate 111 Color Number 13 — Tone k. 3 year wood — Gray — Mouse Gray Plate LI Color 15''''' — Ridgway's Color Standards. Lenticels — Numerous; large.

*Leaves.*—Medium large; ovate; acutely pointed; medium thick; smooth. Length — 7 inches. Width — 1½ inch.

*Color.*—Dark Green — Ivy Green Plate XXXI — Color Number 25'' Tone f — Ridgway's Color Standards.

*Margin.*—Finely serrate.

*Petiole.*—Medium short; thick.

*Glands.*—Average number: 3; alternate; medium small; mixed; appressed.

Flowers:

*Dates of first and full bloom.*—Mar. 23, 1976 and Mar. 30, 1976 respectively; medium early.

*Size.*—Small.

*Color.*—Pink — Munsell Hue 2.5R.

Fruit:

*Maturity when described.*—Eating; Date — July 29, 1976.

*Size.*—Large. Axial diameter — 3 inches. Transverse in suture plane — 3⅛ inches. At right angles to suture plane — 3 inches.

*Form.*—Uniform; globose.

*Suture.*—Shallow; deep at stem end "crowned" on some fruits; extends from base to apex; has slight marked depression beyond pistil point.

*Ventral surface.*—Rounded; strong lipped toward apex on right side; lips unequal.

*Cavity.*—Rounded; suture showing on one side. Depth — 7/16 inch. Breadth — 1 inch.

*Base.*—Rounded.

*Apex.*—Short; rounded; pistil point apical.

*Stem.*—Length — ⅛ inch; stout; pubescent; adherence to stone strong.

*Skin.*—Thick; tough; astringent; tenacious to flesh; tendency to break — none. Color — Highly blushed red — Pompeian Red Plate XIII — Color Number 3' Tone i — Ridgway's Color Standards. Down — Scant; short; does not roll up when rubbed.

*Flesh.*—Color — Yellow — light cadmium Plate IX — Color 19 — Ridgway's Color Standards; mottled with red next to stone.

*Surface of pit cavity.*—Red — Rose Doree Plate 1 — Color No. 3 Tone b — Ridgway's Color Standards.

*Amygdalin.*—Wanting; moderate juice.

*Texture.*—Firm.

*Fibers.*—Few; fine; tender.

*Ripens.*—Fairy even.

*Flavor.*—Mild.

*Aroma.*—Distinct.

*Eating quality.*—Good.

Stone: Free.

*Fibers.*—Short, parts from flesh smoothly; retains short fiber like threads along ridges.

*Size.*—Large. Length — 1½ inch. Thickness — ⅞ inch.

*Form.*—Oval; full; cunate toward base.

*Base.*—Straight; narrow; oval.

*Apex.*—Acute.

*Sides.*—Equal.

*Surface.*—Furrowed toward apex; pitted throughout.

*Ridges.*—Rounded toward base.

*Pits.*—Circular.

*Dorsal edge.*—Full; with deep broad groove throughout; ridges on either side; continuous.

Use: Market; local; dessert; canning.

Keeping quality: Good.

Resistance to diseases: Resistant to Bacterial leaf spot.

Shipping quality: Good.

General notes: Similar to Early Rio Oso Gem variety (U.S. Plant Pat. No. 2,940) except that it ripens approximately 8 days earlier.

I claim:

1. A new and distinct variety of peach tree, which originated as a whole tree mutation of the Rio Oso Gem variety substantially as illustrated and described, which bears fruit which ripens approximately 17 to 18 days earlier than that of the Rio Oso Gem variety and approximately 8 days earlier than that of the Early Rio Oso Gem variety.

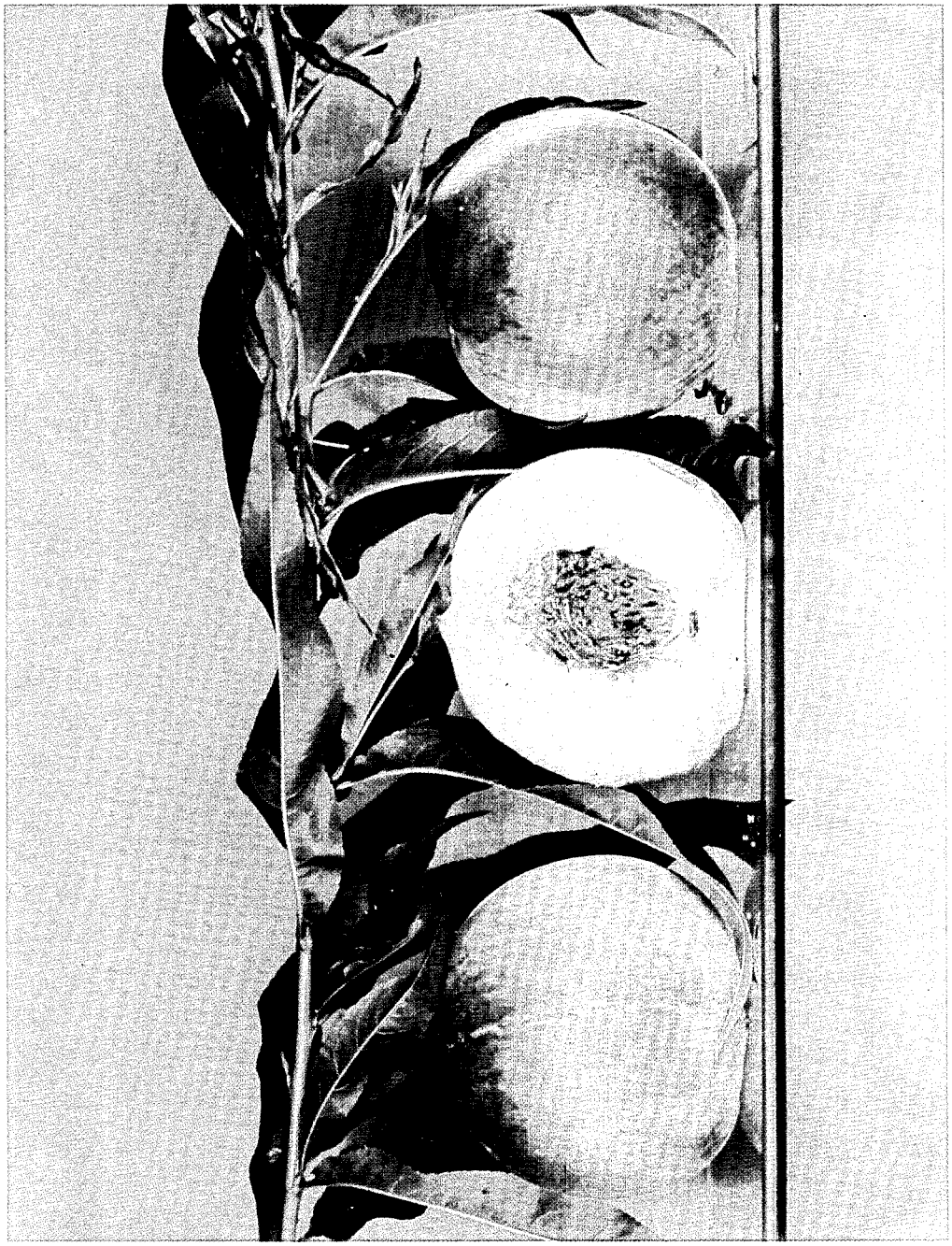

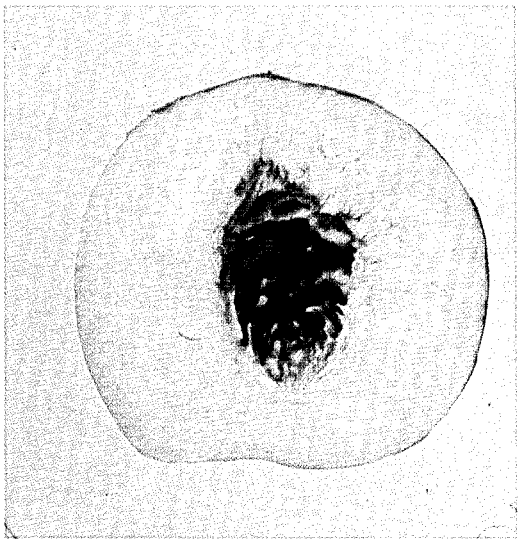

* * * * *